United States Patent [19]

Hoffman

[11] Patent Number: 5,682,038
[45] Date of Patent: Oct. 28, 1997

[54] FLUORESCENT-PARTICLE ANALYZER WITH TIMING ALIGNMENT FOR ANALOG PULSE SUBTRACTION OF FLUORESCENT PULSES ARISING FROM DIFFERENT EXCITATION LOCATIONS

[75] Inventor: Michael A. Hoffman, Carmel, Calif.

[73] Assignee: Becton Dickinson and Company, Franklin Lakes

[21] Appl. No.: 417,744

[22] Filed: Apr. 6, 1995

[51] Int. Cl.[6] .................. G01J 1/58; G01J 3/51; G01N 21/64; G01N 33/48
[52] U.S. Cl. .................. 250/458.1; 250/459.1; 250/462.1; 250/226; 356/39; 356/411
[58] Field of Search ............... 250/458.1, 459.1, 250/462.1, 226; 356/411, 39; 348/343, 344

[56] References Cited

U.S. PATENT DOCUMENTS

| | | | |
|---|---|---|---|
| 4,573,796 | 3/1986 | Martin et al. | 356/318 |
| 5,150,313 | 9/1992 | Engh et al. | 364/569 |
| 5,168,164 | 12/1992 | Urakami et al. | 250/458.1 |
| 5,270,548 | 12/1993 | Steinkamp | 250/458.1 |

OTHER PUBLICATIONS

"Improved Multilaser/Multiparameter Flow Cytometer For Analysis And Sorting Of Cells And Particles," by John A. Steinkamp, et al., Rev. Sci. Instrum. 62 (11), Nov. 1991, pp. 2751–2764.

"Cytomat–R: A Computer–Controlled Multiple Laser Source Multiparameter Flow Cytophotometer System," Authors: Howard M. Shapiro, et al., The Journal of Histochemistry and Cytochemistry, vol. 25, No. 7, pp. 836–844, 1977.

"A Generalized Machine For Automated Flow Cytology System Design," Authors: Raul Curbelo, et al., The Journal of Histochemistry And Cytochemistry, vol. 24, No. 1, pp. 388–395, 1976.

"Internal Calibration To Absolute Values in Flowthrough Particle Size Analysis," Authors: W.G. Eisert, et al., Rev. Sci. Instrum., 49(12), Dec. 1978, pp. 1617–1621.

"Laser Flow Cytometric Light Scatter And Fluorescence Pulse Rise–Time Sizing of Mammalian Cells[1]," Authors: James F. Leary, et al., The Journal of Histochemistry and Cytochemistry, vol. 27, No. 1, pp. 315–320, 1979.

"A Real–Time Delay Monitor For Flow–System Cell Sorters[1]," Authors: J.C. Martin, et al., The Journal of Histochemistry and Cytochemistry, vol. 27, No. 1, pp. 277–279, 1979.

*Primary Examiner*—Michael J. Tokar
*Assistant Examiner*—Virgil Orlando Tyler
*Attorney, Agent, or Firm*—Allen W. Wark, Esq.

[57] ABSTRACT

A flow cytometry system includes a flow tube through which particles marked with different fluorochromes pass from a first location, illuminated by a red laser, to a second location, illuminated by a blue laser. A "red" photodetector is optically coupled to detect red fluorescence from both locations. "Yellow" and "green" photodetectors respectively detect yellow and green fluorescence from the second location, while a "scattered light" detector detects scattered light from the second location. During a sample run, the red photodetector can output pulses that correspond primarily to APC fluorochrome at the first location and to PerCP at the second location respectively. A delay device delays the APC pulse relative to the PerCP pulse so that the peaks can be scaled and subtracted in the analog electrical domain to remove APC/PerCP crosstalk. The delay is calibrated using a set of APC tagged cells. Each of these cells generates a red fluorescence electrical pulse while at the first location and a scattered light pulse while at the second location. The average time differential between these two pulses for the set of timing cells determines the target delay. This is compared with the actual delay imposed by the delay device. If the error is greater than 0.5 µS, the imposed delay can be adjusted until the delay is below 0.5 µS, or within the tolerance required for reliable difference pulses to be generated by the pulse subtractor.

5 Claims, 2 Drawing Sheets

FLUORESCENT-PARTICLE ANALYZER WITH TIMING ALIGNMENT FOR ANALOG PULSE SUBTRACTION OF FLUORESCENT PULSES ARISING FROM DIFFERENT EXCITATION LOCATIONS

BACKGROUND OF THE INVENTION

The present invention relates to optical instruments and, more particularly, to instruments for distinguishing and quantifying emissions from fluorescent particles. A major objective of the present invention is to reduce crosstalk in the detection of fluorochrome when more than one excitation laser is used.

Research and testing laboratories need to be able to detect the presence of certain entities, such as antigens, that can be difficult to detect directly. In some cases, the entities can be tagged with fluorochromes which are detectable. For example, an antibody for an antigen can be derivatized with a fluorochrome. The derivatized antibody can be mixed with a blood sample. To the extent the antigen is present in a cell, the derivatized antibody binds to it so that the incorporating blood cell is rendered fluorescent. The fluorescent cells can be introduced in a cytometry system, wherein they can then be illuminated with monochromatic laser radiation that excites the fluorochrome. A photodetector can then detect the intensity of the fluorescence.

It is often necessary to identify blood cells containing a particular combination of antigens. To this end, several antibodies can be tagged with respective fluorochromes and then bound to the respective antigens. The cells are then illuminated, and the resulting fluorescent emissions are detected and measured.

To the extent possible, the fluorochromes are chosen to have distinct emissions spectra. A typical fluorescent analyzer can include a blue laser to excite fluorochromes that emit green, yellow, and red light, respectively. Dichroic mirrors or other wavelength-dispersive elements can split the emissions into green, yellow and red beams that are directed to respective photodetectors. In practice, it is difficult to distinguish more than three fluorochromes by wavelength alone due to overlap in emissions spectra.

The number of distinguishable fluorochromes can be increased by using more than one excitation wavelength. This approach takes advantage of the fact that fluorochromes differ not only in their emissions spectra, but also in their excitation spectra. In an ideal case, two fluorochromes with non-overlapping excitation spectra could be distinguished even where the emissions spectra were identical. The distinction could be achieved by illuminating the fluorochromes at different times with two lasers, each selected to excite only a respective one of the fluorochromes. The resulting emissions would appear as two distinct pulses in the output of a single photodetector.

This approach is implemented in the context of a flow cytometry system by illuminating different locations along the flow tube with different laser wavelengths, each of which preferentially excites a respective fluorochrome, e.g., PerCP and APC. Tagged cells are made to flow serially past the two locations. When a cell is at the first location, a photodetector pulse corresponds to the first fluorochrome; when later the cell is at a second location, a photodetector pulse corresponds to the second fluorochrome. The pulses are routed and at least minimally processed in the analog domain. They are then converted to digital data, which can then be manipulated in the digital domain to provide the desired information about the cells.

In such a flow cytometry system, each pulse generated corresponds predominantly to a respective fluorochrome. Because of overlapping emissions and excitation spectra, each pulse can include contributions, i.e., "crosstalk", from other fluorochromes. Two types of crosstalk can be distinguished: "intrabeam" crosstalk results from overlap in the emissions spectra of fluorochromes excited by a common laser beam; "interbeam" crosstalk results from the overlap in the excitation spectra of fluorochromes excited by different laser beams. There are optical techniques for reducing both types of crosstalk, but they are incomplete. Accordingly, post-detection correction of crosstalk is required.

The mathematics of crosstalk reduction is well understood. In general, crosstalk can be removed from a measurement primarily corresponding to one fluorochrome by subtracting a crosstalk term that is a function of measurements primarily corresponding to the other fluorochromes. More specifically, the crosstalk term can be a sum of product terms; each product term is a fluorochrome measurement multiplied by a coefficient. The coefficients can be determined empirically during a calibration run.

It is straightforward to implement crosstalk reduction digitally. The photodetector output is digitized; the resulting data can be manipulated to obtain raw fluorochrome measurements, which can be combined as required for crosstalk reduction. Some flow cytometry systems shift some of the processing required for intrabeam crosstalk reduction to the analog domain. For example, an analog peak holder or integrator can provide single values that can be sampled once by an analog-to-digital converter instead of the many times required for peak detection or integration in the digital domain. In addition, subtraction of time-coincident pulses in the analog domain relieves the burden on the digital processor.

Intrabeam crosstalk reduction is an task that has proved well-suited for analog processing. In a single laser system, all fluorochromes are excited and thus detected at the same time. Thus, pulses corresponding to the different fluorochromes associated with a particular cell or other particle are generated simultaneously. These pulses are entered into a subtractor that subtracts crosstalk from fluorochromes with significantly overlapping emissions spectra. In a three fluorochrome system, crosstalk between the two extreme emissions spectra can often be ignored so that each fluorochrome pulse has crosstalk from only one other fluorochrome pulse subtracted from it to yield a crosstalk-free pulse. The corrected pulses are then processed by a peak holder so that they assume a constant value which can be sampled at a relatively low rate by an analog-to-digital converter. Thus, the digital processor receives a single crosstalk-corrected quantity for each pulse.

Analog interbeam crosstalk reduction must address the fact that the pulses resulting from different excitation beams are generated at different times. This problem can be addressed by inserting a delay device in the path of an earlier generated fluorescence pulse that delays a pulse by the time required for the particle to flow from the first excitation location to the second excitation location. However, in the course of the present invention, it was determined that systems incorporating analog interbeam crosstalk reduction can have inaccurate results. What is needed is an improvement that improves the reliability of analog interbeam crosstalk reduction.

SUMMARY OF THE INVENTION

The present invention applies to a fluorescent-particle analyzer having: 1) a pair of lasers or another excitation source for illuminating first and second excitation locations; 2) a flow tube or other means for guiding particles past the first location and then past the second location; 3) optics for directing fluorescence from the particles as stimulated at the first and second locations; 4) one or more photodetectors for generating pulses in response to respective detections of radiation, including fluorescence, from the first and second locations; 5) a delay device for delaying a pulse generated while a particle is at the first location relative to a pulse generated while the same particle is at the second location; and 6) a pulse subtractor for correcting crosstalk in at least one of said pulses by subtracting a contribution indicated by the other of the pulses. The analog output of the system can be digitized for subsequent data processing.

The present invention provides for detection of a delayed first timing pulse arising from radiation detected from the first location and an undelayed second timing pulse resulting from radiation detected from the second location. Preferably, indications are provided for leading and trailing pulse transitions through predetermined thresholds. The thresholds can be set independently for the delayed first timing pulse and the undelayed second timing pulse. Alternatively, peak detection can be used.

A controller determines a timing error from these pulse detections. For example, the times associated with leading and trailing transition indications can be averaged for each delayed first timing pulse and each undelayed second timing pulse. The averages are compared to yield a timing error for the associated timing particle. The timing error can be averaged over many particles to remove particle-to-particle timing variations. The time-averaged error is compared with an error tolerance. If the error exceeds the tolerance, the delay device is adjusted to reduce the error below the tolerance. Optionally, an excessive error can be flagged to a human operator who can decide when to adjust the delay.

The present invention can be applied during a dedicated calibration run in a "calibration mode", or can be used to regulate the delay device during a sample run. In the latter case, sample particles can serve as the timing particles. In the former case, specially prepared particles can be used for timing purposes. For example, the fluorescence of the timing particles can be predetermined.

Where the first and second fluorescent pulses are generated at the same photodetector output, there is a potential for the subtractor to operate on the undelayed first fluorescence pulse and/or on a superfluously generated delayed second fluorescence pulse. The preferred method of handling this problem is to gate the output of the subtractor to eliminate the leading undelayed first fluorescence pulse, to allow the coincident pulses to pass, and then to eliminate the delayed second fluorescence pulse. An alternative is to demultiplex the photodetector output so that the undelayed first fluorescence pulse does not reach the subtractor and so that the delayed second fluorescence pulse is not generated.

In either case, the gating or the switching must be timed. Preferably, gating or switching is initiated by a detection that is associated with the second excitation location. Alternatively, gating or switching can be timed relative to a detection at the first location. In either case, the challenge is to distinguish the desired double-detection of one particle from two single detections of two particles that are not well separated in the particle stream. Thus, the pulse used for gating or switching should be uniquely associated with a selected one of the two excitation locations.

The present invention ensures that the pulses being subtracted are sufficient concurrent that the difference pulse output by the subtractor can serve as an accurate crosstalk-corrected representation of the quantity of a respective fluorochrome. Without the present invention, changes in particle flow rate and/or the delay itself could cause the delayed first fluorescence pulse to arrive at the subtractor at a different time that the undelayed second fluorescence pulse. In that case, the resulting difference pulse would not have crosstalk reduced optimally.

Another advantage of the present invention is that it can be implemented with minimal changes to existing flow cytometry systems. These and other features and advantages of the present invention are apparent from the description below with reference to the following drawings.

DESCRIPTION OF THE PREFERRED EMBODIMENTS

Figure 1:
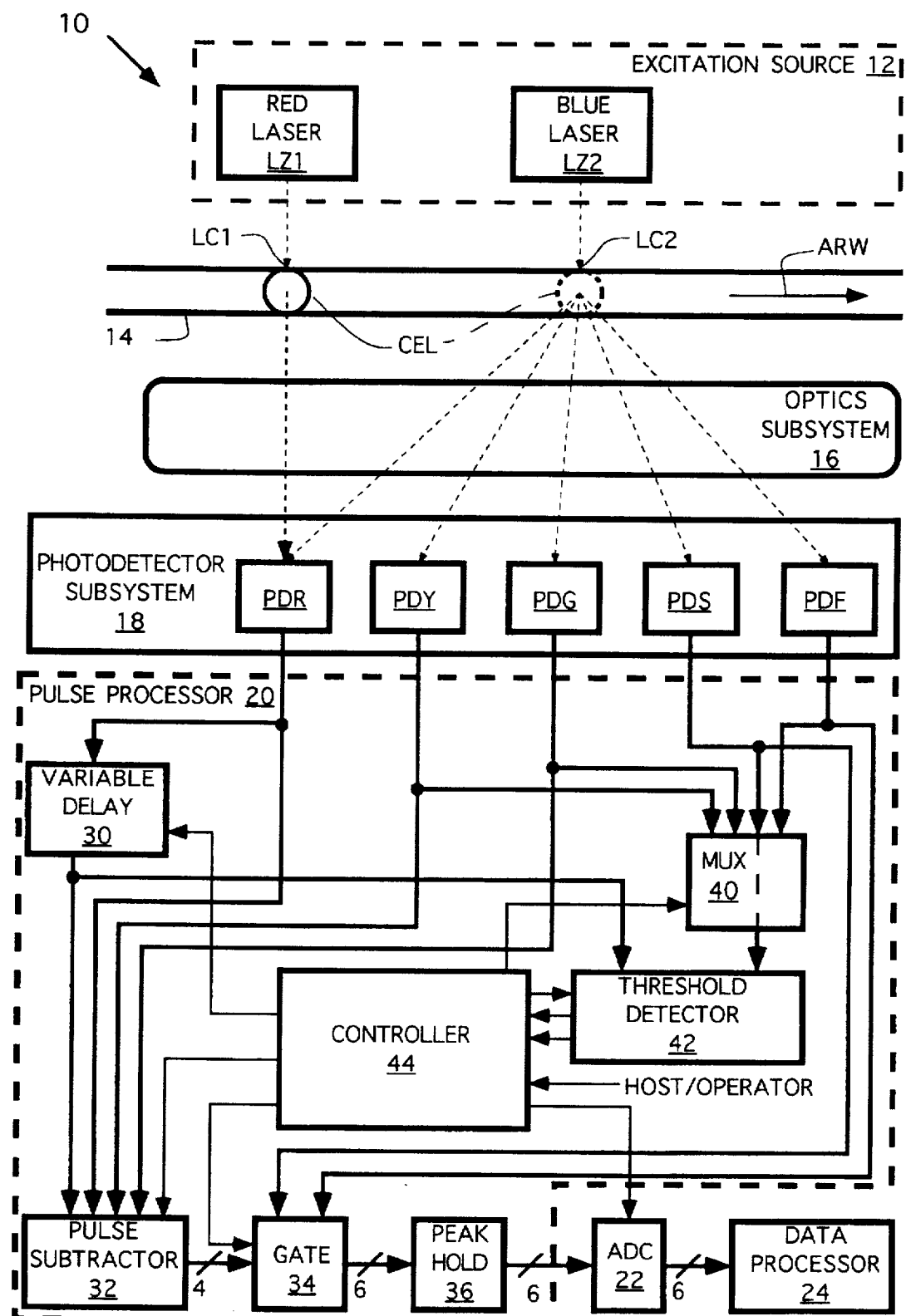
FIG. 1 is a schematic view of a flow cytometry system in accordance with the present invention.

In accordance with the present invention, a flow cytometry system 10 for characterizing a blood cell CEL comprises a laser source 12, a flow tube 14, an optical subsystem 16, a photodetector subsystem 18, an analog pulse processor 20, an analog-to-digital converter 22, and a digital data processor 24. Laser source 12 includes a red laser LZ1 and a blue laser LZ2. Photodetector subsystem 18 includes five photodetectors, a "red-fluorescence" photodetector PDR, a "yellow-fluorescence" photodetector PDY, a "green-fluorescence" photodetector PDG, a side-scattered light detector PDS, and a forward-scattered light detector PDF. Analog pulse processor 20 includes a variable delay 30, an analog pulse subtractor 32, a six-channel gated amplifier 34, and six-channel peak holder 36, a four-to-one multiplexer 40, a two-channel threshold detector 42, and a controller 44.

A function of flow cytometry system 10 is to determine which, if any, of four antigens are carried by blood cells, including cell CEL. To this end, respective antibodies for the antigens are derivatized with respective fluorochromes allophycocyanin (APC), peridinin chlorophyl protein (PerCP), fluorescein isothiocyanate (FITC), and R-phycoerythrin (RPE). The blood cells are incubated with a mixture of these derivatized antibodies under conditions sufficient for antibodies to bind with their respective antigens to tag the blood cells. In general, any fluorescence emitted by cells is readily distinguished from any background fluorescence contributed by unbound antibodies; where this is not the case, the unbound antibodies can be washed away prior to fluorescence analysis of the cells. The tagged blood cells are then serialized in a stream flowing through flow tube 14, which guides movement of timing particles and sample cells, including cell CEL, past flow-tube locations LC1 and LC2 in the direction indicated by flow arrow ARW.

To excite the fluorochrome-tagged cells, lasers LZ1 and LZ2 provide highly monochromatic light to respective flow-tube "excitation" locations LC1 and LC2, which are about 120 microns apart. Laser LZ1 is a diode laser that provides 635 nm red radiation. Alternatively, 633 nm red light can be provided by a more expensive helium-neon laser for a more Gaussian beam. Laser LZ2 is an argon ion laser that provides 488 nanometer (nm) blue light. Although shown otherwise for illustrative purposes, lasers LZ1 and LZ2 are preferably directed orthogonal to the direction along which emissions are detected to minimize noise in the detection signals.

When cell CEL reaches flow-tube location LC1, the incident red light from laser LZ1 strongly excites any present APC fluorochrome, at most weakly exciting PerCP, FITC, and RPE fluorochromes. Emissions from location LC1 are directed to red-fluorescence photodetector PDR by optics subsystem 16. Optics subsystem 16 conventionally includes dichroic mirrors that separate emissions by wavelength ranges (red, yellow, green) into beams directed respectively to photodetectors PDR, PDY and PDG. Thus, optics subsystem 16 primarily directs red APC to red photodetector PDR.

When cell CEL reaches flow-tube location. LC2, any PerCP, FITC, and RPE fluorochromes are strongly excited, while any APC is at most weakly excited. The dichroic mirrors of optics subsystem 16 split emissions by wavelength so that green, predominantly FITC, emissions are directed to photodetector PDG, so that yellow, predominantly RPE emissions, are directed to photodetector PDY, and so that red emissions, which are predominantly PerCP, are directed to photodetector PDR. In addition, optics subsystem 16 collects blue light from laser LZ2 that is scattered laterally for detection by side-scatter photodetector PDS. Optics subsystem 16 also collects blue light from laser LZ2 that is scattered in a forward direction (but off the main beam) to be detected by forward-scatter photodetector PDF; optics subsystem 16 occludes the main beam from laser LZ2 from photodetector PDF. Each photodetector outputs an electrical pulse when a respective detection is made.

The photodetector outputs from photodetector subsystem 18 are directed to analog pulse processor 20. The outputs of fluorescence photodetectors PDR, PDY and PDG are coupled to respective first, second and third inputs of four-by-four pulse subtractor 32. The output of fluorescence photodetector PDR is also coupled to the input of variable delay 30, the output of which is coupled to a fourth input of pulse subtractor 32. Thus, a delayed APC pulse arrives at subtractor 32 at the same time as undelayed PerCP, RPE and FITC pulses. In addition, an undelayed APC pulse arrives before the others and a delayed PerCP pulse arrives after the others; any effects of these superfluous pulses on the outputs of subtractor 32 are eliminated by gate 34.

Ideally, crosstalk reduction would involve subtracting from each fluorescence pulse fractions of each of the other pulses arriving contemporaneously at subtractor 32. In other words, the following equations apply $$V_{FITC(corrected)} = C_{FITC}V_{FITC} - (C_{RPE}^{FITC}V_{RPE} + C_{APC}^{FITC}V_{APC} + C_{PerCP}^{FITC}V_{PerCP})$$

$$V_{RPE(corrected)} = C_{RPE}V_{RPE} - (C_{FITC}^{RPE}V_{FITC} + C_{APC}^{RPE}V_{APC} + C_{PerCP}^{RPE}V_{PerCP})$$

$$V_{APC(corrected)} = C_{APC}V_{APC} - (C_{RPE}^{APC}V_{RPE} + C_{PerCP}^{APC}V_{PerCP} + C_{FITC}^{APC}V_{FITC})$$

$$V_{PerCP(corrected)} = C_{PerCP}V_{PerCP} - (C_{APC}^{PerCP}V_{APC} + C_{RPE}^{PerCP}V_{RPE} + C_{FITC}^{PerCP}V_{FITC})$$

where the Vs on the left sides of the equations are values of fluorescence pulses corrected for crosstalk, and Vs on the right sides of the equations are pulse values as input to subtractor 32. The minuend (nonsuperscripted) coefficient Cs represent optionally scaling to be applied to the minuend pulse (for example, to compensate for nonuniformities in detector sensitivity) from which the other scaled pulses are to be subtracted. The minuend coefficients are necessarily positive and are typically set equal to unity; i.e., in practice, the minuend pulses are not scaled.

The subtrahend (superscripted) coefficient Cs represent the empirically determined contribution of the fluorochrome indicated in the subscript to the pulse associated with the fluorochrome indicated in the superscript. Subtrahend coefficients are predominantly positive and less than unity, since the net effect of the subtrahend terms is to remove crosstalk from the minuend term. (Thus, crosstalk reduction typically involves subtracting a fraction of one pulse from another pulse.) However, since subtrahend terms can also include crosstalk components, subtracting them can overly compensate for crosstalk in the subtrahend term. Accordingly, some subtrahend coefficients can be negative to offset this overcompensation.

The subtrahend coefficients can be determined empirically using known calibration procedures. Most of the subtrahend coefficients are dependent on the relative gain of the photomultipliers. The relative gain between pulses detected by the same photomultiplier does not change, so the coefficients for the respective fluorochromes are less dependent on instrument settings. Thus, the coefficients $$C_{PerCP}^{APC} \text{ and } C_{APC}^{PerCP}$$

are both about 0.05, independent of the gain of photodetector PDR.

$$C_{FITC}^{RPE}$$

tends to vary in the range of 0.1 to 0.3;

$$C_{RPE}^{FITC}$$

tends to vary in the range from 0.01 to 0.02. The remaining subtrahend coefficients tend to be smaller; for this reason, the respective subtrahend terms often ignored in practice, effectively setting these coefficients to zero.

Once the coefficients are set, pulse subtractor 32 performs these four subtractions on throughgoing pulses, providing the respective differences at respective outputs. Each of the difference pulses output from subtractor 32 corresponds to the value of the emissions due to a respective fluorochrome corrected for crosstalk. The outputs of subtractor 32 are provided to four of the six pulse inputs six-channel gate 34. The other two pulse inputs of six-channel gate 34 are respectively coupled to the outputs of scattered light photodetectors PDS and PDF. Gate 34 allows pulses to pass while a cell is at location LC2, but is off otherwise to reject spurious pulses. The rejected pulses not only include random noise, but also artifacts produced by analog pulse subtractor 32 as it processes the undelayed APC and the delayed PerCP pulse from variable delay 30.

The six outputs from gate 34 are input to six-channel peak holders 36. The held peaks output from six-channel peak holder 36 are converted to respective digital values by six-channel analog-to-digital converter 22. The six peak values output from six-channel analog-to-digital converter 22 are then processed by digital data processor 24, which uses the digital peak readings to identify and quantify fluorochromes, and thus antigens. In alternative embodiments, a six-channel pulse integrator is used instead or in addition to peak holder 36.

At a typical flow rate, cells pass from flow-tube location LC1 to flow-tube location LC2 in about 20 microseconds ($\mu$S). Accordingly, variable delay 30 is set to impose a delay of about 20 microseconds. However, if due to variations in flow rate or in the delay imposed by delay 30, the electrical delay and the flow delay are not matched, the delayed first fluorescent peak and the undelayed second fluorescent peak will not be properly aligned. As a result, analog pulse subtractor 32 can give inaccurate results. Accordingly, the present invention provides for calibrating and/or regulating the delay imposed by variable delay 30.

Variable delay 30 can be set to impose a delay equal to the delay between a detection of a particle at location LC1 and a detection of the same particle at location LC2. Since only photodetector PDR is optically coupled to location LC1, its output is necessarily used for detecting the particle at location LC1. Since all five photodetectors are optically coupled to location LC2, any of them could be used for the detection at location LC2. However, to avoid an ambiguity between the detection of the same particle at location LC2 and a detection of a closely following particle at LC1, fluorescence analyzer 10 precludes use of a pulse output from photodetector PDR for the second timing pulse. The other four photodetectors have their outputs coupled to respective inputs of a multiplexer 40, the setting of which determines which photodetector provides the second timing pulse. Note that this means that the second timing pulse can be the result of fluorescence or scattered light.

The timing of the first timing pulse (due to fluorescence from location LC1) relative to the second timing pulse (due to fluorescence or scattering at location LC2) is determined with the help of threshold detector 42. Threshold detector 42 has a first input coupled to the output of variable delay 30 and a second input coupled to the output of multiplexer 40. Thresholds are set independently for the two inputs. Threshold detector 42 indicates when the leading and trailing transitions of an as-delayed timing pulse from delay 30 cross the first input threshold; the two indications for each first timing pulse are output to a first output of threshold detector 42. Threshold detector 42 indicates when the leading and trailing transitions of an undelayed timing pulse from multiplexer 40 cross the second input threshold; these two indications from the second timing pulse are output from a second output of threshold detector 42. Both outputs of threshold detector 42 are coupled to respective inputs of controller 44.

Controller 44 determines an error between as-delayed first timing pulses and undelayed second timing pulses. For each timing pulse, the times at which the leading and trailing threshold crossing are indicated are averaged to determine a time associated with the pulse peak. For each pair of first and second timing pulses, the peak times are subtracted. This difference is averaged over a statistically reliable number, e.g., twenty, of timing particles to provide the error. If the error is greater than a predetermined tolerance, e.g., 0.5 μS, controller 44 can adjust delay 30 to reduce the error to within the tolerance.

Controller 44 also derives the timing for gate 34 and analog-to-digital converter 22 from the indications provided by threshold detector 42. Controller 44 also communicates with a host computer. An operator can use the host computer to communicate coefficients for subtractor 32 and the operator's selection for the source of the second timing pulse (i.e., the setting of multiplexer 40).

Controller 44 can indicate to the host computer that a timing error has been found, allowing a calibration mode of operation in which the operator decides whether to correct the error or not. In an alternative regulation mode, the corrections are made automatically.

Typically, scattered light pulses, either from photodetector PDS or PDF, are used for timing purposes so that second timing pulses are generated whether or not the timing particles are fluorescent. In the preferred embodiment, there is only a red photodetector PDR optically coupled to flow-tube location LC1. Thus, the preferred timing particles are blood cells tagged with APC. However, the timing particles need not be blood cells; for example, fluorescent latex particles can be used for timing calibration.

In the preferred calibration mode, a set of APC-stained cells are flowed past locations LC1 and LC2. Red fluorescence excited at location LC1 is detected by photodetector PDR and delayed by variable delay 30; the resulting timing pulse is directed to one threshold detector input. The first threshold detector 42 detects a leading transition of the first timing pulse and then a trailing transition of the same pulse. The threshold at which the detections are made is set automatically to be just above a noise floor for the output of photodetector PDR. The transition detections are fed to controller 44, which thus assigns times t1 and t2 to these transitions.

The subsequent scattered light (or green or yellow fluorescence) detection at flow-tube location LC2 is routed to the other input of threshold detector 42. Threshold detector 42 provides indications of the leading and trailing transitions in the second timing pulse. The threshold at which transitions are detected is set manually by a human operator, preferably to be above the noise floor of the scattered light photodetectors PDS and PDF. The transition indications for the second timing pulse are fed to controller 44, which assigns times t3 and t4 to these indications.

Due to the relative symmetry of detection pulses, the peak of the first timing pulse can be found midway between leading and trailing threshold crossings, so a time t5=(t2−t1)/2 can be associated with the peak of the first timing pulse and a time t6=(t4−t3)/2 can be associated with the peak of the second timing pulse. t6−t5 then yields a timing error for the individual particle. This interval is averaged over several calibration cells to yields a time-averaged timing error. In other words, the timing error ε averaged over N calibration cells dyed with APC is given by:

$$\epsilon = \frac{1}{2N} \sum_{i=1}^{N} (ti2 + ti3 - ti1 - ti4)$$

This timing error is compared to a timing error tolerance. If the error is greater than the tolerance, the delay is adjusted to reduce the error below the tolerance. If the error is not greater than the tolerance, no adjustment is made. The tolerance is set low enough that the subtraction results are accurate; for example, a timing error greater than 1.0 μS can lead to misleading differences being output from subtractor 32. The tolerance is set high enough that the delay is not changed too frequently; for example, an adjustment made in a calibration run should not require further adjustment during the next sample run. A practical value for the timing error tolerance is 0.5 μS.

An alternative is to compare the undelayed first timing pulse with the undelayed second timing pulse to determine the transit time for a particle to move from excitation location LC1 to excitation location LC2. A controller can compare this transit time with the delay imposed on the first timing pulse to determining a timing error, which is corrected as above. The disadvantage of this approach is the variations in the delay device itself are not accounted for.

Instead of the calibration mode, the operator can select a "regulation" mode in which the delay is regulating during a sample run without further operator intervention. During the course of a sample run, controller 44 looks for a pair of detections from threshold detector 42 to be followed by a pair of detections from threshold detector 42. When this pattern is found, the flow time represented is recorded. After twenty such pairs, the flow times are averaged and used to determine whether delay 30 requires adjustment or not. If adjustment is required, it is performed without operator intervention in the regulation mode.

Note that when a fluorescence detection is used for a timing signal, timing cells must be tagged with the corresponding fluorochrome. Where both timing pulses are based on fluorescence detections, each timing particle should be tagged with two fluorochromes, although it is possible a single fluorochrome could yield the desired emissions at each flow-tube excitation location.

Figure 2:
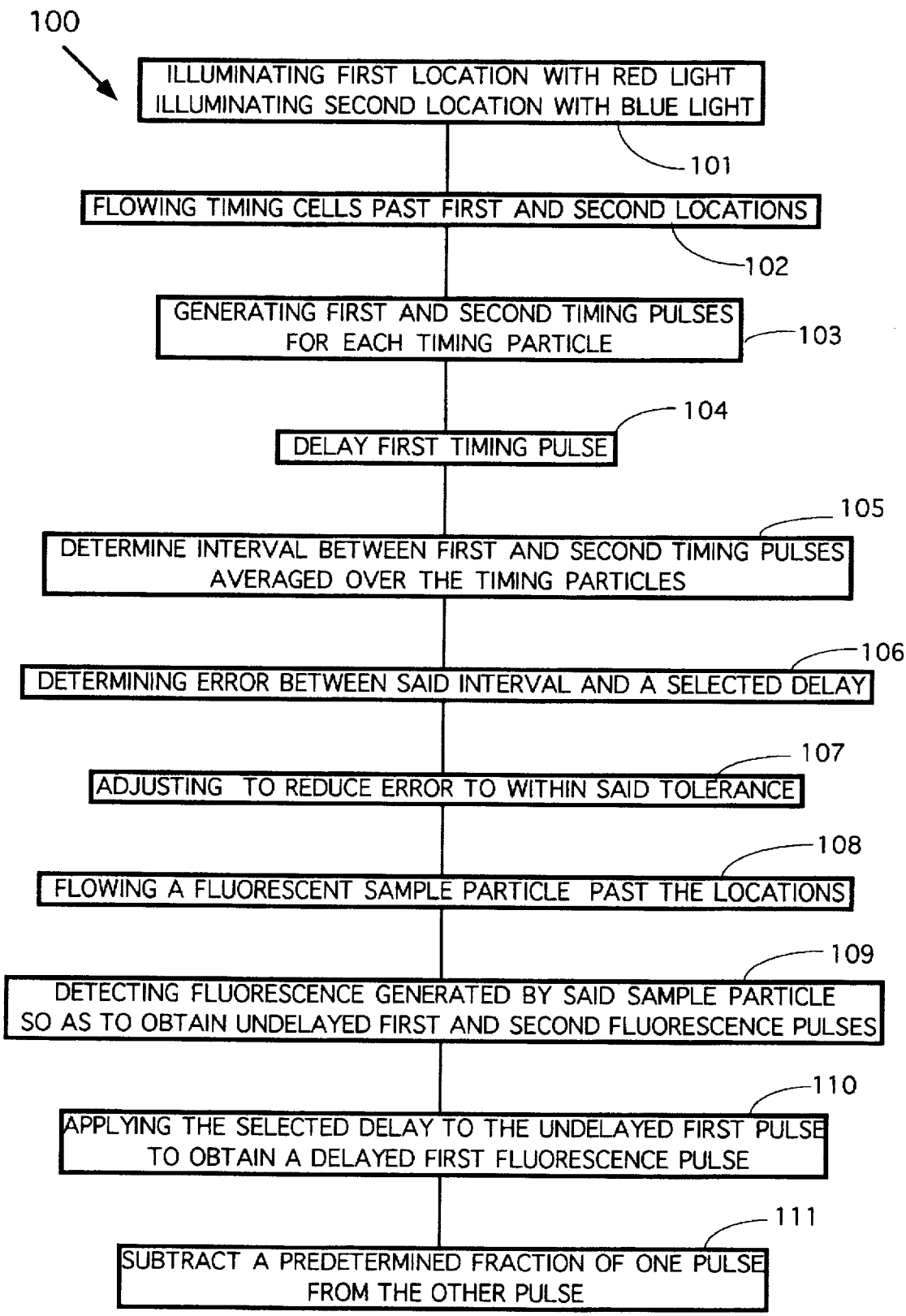
FIG. 2 is a flow chart of a method practiced in the operation of the system of FIG. 1.

The method 100 detailed above is summarized in the flow chart of FIG. 2. At step 101, the first location is illuminated with red light and the second location is illuminated with blue light. At step 102, timing cells are flowed in succession past the two locations; the timing cells are preferably tagged with APC. At step 103, as the timing cells pass the locations, the photodetector (PDR) generate pairs of timing pulses. Each pair includes an undelayed first timing pulse based on a detection of APC emissions at the first location and an undelayed second timing pulse based on a detection of PerCP emissions from the second location. At step 104, the first timing pulses are delayed by the selected delay amount.

At step 105, the interval (peak-to-peak) between the delayed first and the undelayed second pulses is determined for each timing pair of pulses. The interval is averaged over all the timing pairs to yield an error. (Alternatively, the intervals between undelayed first and undelayed second timing pulses can be time averaged to determine a target delay which is compared to the set delay to yield the error.) At step 106, this target delay is compared with the actual delay set for delay 30. At step 107, if the error exceeds a predetermined tolerance, controller 44 changes the actual delay to reduce the error within a predetermined timing tolerance.

At step 108, a sample particle is flowed past the two locations. At step 109, red fluorescence is detected from both locations, yielding a pair of undelayed fluorescence pulses at the output of photodetector PDR. At step 110, the first undelayed fluorescence pulse is delayed by delay 30 to yield a delayed first fluorescence pulse that coincides in time with the undelayed second fluorescence pulse. At step 111, the previously described subtractions (with appropriate scaling) are performed to yield fluorescence pulse corrected for crosstalk.

The disclosed crosstalk reduction on analog pulses can be supplemented by optical techniques for minimizing crosstalk. Crosstalk reduction in the optical domain can be implemented without an additional photodetector as taught in a concurrently filed U.S. patent application entitled "Fluorescence Particle Analyzer with Spatially Split Wavelength Filter" by Robert A Hoffman and William Treyfl. To this end, optics subsystem 14 includes a split wavelength filter, a collection lens, and spatial filter with two apertures.

The split wavelength filter is located optically between flow-tube excitation locations LC1 and LC2 and photodetector PDR. The split filter includes a low-pass wavelength filter and a high-pass wavelength filter, both with cutoffs midway between the emissions' spectra peaks for APC and PerCP. (The low-pass wavelength filter is a high-pass frequency filter; likewise, the high-pass wavelength filter is a low-pass frequency filter.) The collection lens images location LC1 at the low-pass wavelength filter and images location LC2 at the high-pass filter. The spatial filter has one pin hole aligned with each image location to enhance optical isolation of the emissions from excitation locations LC1 and LC2.

Thus, the low-pass wavelength filter preferentially passes APC emissions, which are strongly excited at excitation location LC1, at the expense of PerCP emissions, which are weakly excited at location LC1; likewise, the high-pass wavelength filter preferentially passes PerCP emissions, which are strongly excited at excitation location LC2, at the expense of APC emissions that are weakly excited at location LC2. Thus, the first of a pair of fluorescence pulses output from photodetector PDR represents APC emissions with some PerCP crosstalk removed, while the second pulse of the pulse pair represents PerCP emissions with some APC crosstalk removed. Thus, the crosstalk that must be handled by analog pulse processor 20 is reduced.

While a preferred embodiment has been described above, the present invention provides for a range of alternatives. The invention requires at least two excitation locations. However, there can be more. The invention can be applied to any pair of three or more excitation locations. Furthermore, three-way crosstalk and "greater-way" crosstalk can be handled among three or more excitation locations using two or more delay devices in parallel.

The different locations can be excited by respective lasers. Alternatively, a single laser can provide excitation for two or more locations, e.g., using a beam splitter. Other excitation sources, such as a Xenon flashlamp can be used. Wavelength dispersive, selective, or shifting elements can be used so that the two locations are excited by different wavelengths. Alternatively, two locations can be excited by the same wavelength. In this case, emissions can be differentially filtered to emphasize one fluorochrome at the first location and another fluorochrome at the second location.

It is important that at least one timing signal be such that it can have been generated from a unique location. In the preferred embodiment, this requirement is met by relying on a scattered light detector that is only coupled to the second location, or by using photodetectors that only receive light in wavelength ranges that could not have been generated at the first flow-tube location. Fluorescence is always at a longer wavelength than the excitation wavelength. The first location is excited by red light, so any resulting fluorescence must be red or infrared. The second location is illuminated by blue light, which can generate blue, yellow, green, and red fluorescence. Since the yellow and green fluorescence cannot have been generated at the first location, detections of green and yellow fluorescence can serve for timing calibration.

In an alternative embodiment, scattered light is detected at both the first and second locations using a second detector. Each passing cell necessarily generates two scattered light detections, and these are relied on primarily for regulating the variable delay for fluorescence detections. The advantage of this approach is that it can be used irrespective of the tagging of the blood cells; this is particularly useful for regulating the delay during a sample run. A disadvantage is the requirement of an additional photodetector. This can be addressed by using an optical fiber to route scattered light from the first location to the detector used to detect light scattered at the second location or to one of the fluorescence photodetectors devoted exclusively to the second location. In the latter cases, the identification of the location from which scattered light was emitted would be essentially unambiguous.

If care is taken to avoid (e.g., by controlling the introduction of cells into the flow tube) or to address (e.g., by detecting such cases and ignoring any ambiguous pulses that result) cases where two cells follow each other closely enough to confuse a second cell at a first location with a first cell at a second location, both timing signals can be taken from the same photodetector. For example, two pulses from a single scattered light detector can be used for timing purposes. Alternatively, two red fluorescence pulses can be used for timing. A threshold detector simply detects four transitions that could be used to compute pulse timing separation.

Subtraction can be performed on the pulses as output from respective photodetectors or after the pulses have been processed. Of course, every device, including delay 30, alters a throughgoing pulse in some manner. However, the present invention provides for intentional pulse transformations prior to subtraction. For example, the peak hold function can be implemented before subtraction. This eases the timing tolerance on pulse alignment. However, performing the subtraction after peak holding can compound errors introduced by the peak holding.

The problem of performing crosstalk reduction before peak holding is related to a limitation of performing crosstalk reduction in the digital domain. The conversion to digital introduces quantization errors, which can be compounded by operations performed in the digital domain. Performing crosstalk reduction in the analog domain as taught by the present invention, can reduce the compounding of quantization errors. On the other hand, the analog crosstalk correction provided by the present invention can be supplemented with further crosstalk reduction in the digital domain.

The present invention also provides embodiment in which superfluous undelayed first fluorescence pulses and delayed second fluorescence pulses are not presented to the analog pulse subtractor. A demultiplexer can route the first pulse to the first input of the pulse subtractor through the delay and then route the second fluorescence pulse directly to the second input of the pulse subtractor. The timing of the router can be determined based on scattered light detections. For example, the routing switch can be triggered either by trailing transition of a scattered light detection at the first flow-tube location or by the leading transition of a scattered light detection at the second flow-tube location.

Instead of relying exclusively on visible light, both longer and shorter wavelength radiation can be used either for excitation and materials that fluoresce in nonvisible radiation ranges can also be employed. Of course, these variations must be accommodated by suitable selection of optical elements and detectors. Herein, "radiation" refers to electromagnetic radiation.

In the context of a flow cytometry system, blood cells are made to pass through stationary laser beams. In the context of a scanning microscope, the laser beams can be moved relative to stationary fluorescent particles. These and other modifications to and variations upon the preferred embodiments are provided for by the present invention, the scope of which is limited only by the following claims.

What is claimed is:

1. A fluorescence analyzer comprising:
    an excitation source for illuminating a first location with a first excitation wavelength and a second location with a second excitation wavelength;
    motion means for relatively guiding a sample particle and timing particles past said first location and then past said second location at a predetermined velocity;
    an optical subsystem for directing radiation from said first and second locations;
    photodetector means for providing pulses in response to changes in said radiation that occur while one of said particles is at one of said locations, said photodetector means providing a first set of undelayed first fluorescence pulses including at least one undelayed first fluorescence pulse when said sample particle is at said first location, said photodetector means providing a second set of second fluorescence pulses including at least one undelayed second fluorescence pulse when said sample particle is at said second location, said photodetector providing first timing pulses at times when one of said timing particles is at said first location, said photodetector providing second timing pulses at times when one of said timing particles is at said second location;
    variable delay means for delaying each undelayed first fluorescence pulse of said first set relative to each undelayed second fluorescence pulse of said second set to yield a set of delayed first fluorescence pulses, said delay means delaying said undelayed first timing pulses to yield respective delayed first timing pulses, said delay means having a delay control input;
    pulse detection means for providing timing indications corresponding to predetermined reference points on said timing pulses, said pulse detection means being coupled to said photodetector means for receiving said first timing pulses and said second timing pulses;
    controller means for adjusting said delay means to control the timing alignment of said set of delayed first fluorescence pulses with respect to said set of undelayed second fluorescence pulses, said controller means being coupled to said delay means for controlling the delay between said each undelayed second fluorescence pulse and said each delayed first fluorescence pulse, said controller means being coupled to said pulse detection means for receiving said timing indications therefrom, said controller means determining a timing error from said timing indications, said controller means adjusting said delay means so as to reduce said timing error when said timing error exceeds a predetermined error tolerance; and
    pulse subtraction means for providing a difference pulse proportional to one of said fluorescence pulses less an amount that varies linearly with said undelayed second fluorescence pulse, said pulse subtraction means having at least a first input coupled to said delay means for receiving said delayed first set, said pulse subtraction means having at least a second input to said photodetector means for receiving said second set.

2. A system as recited in claim 1 wherein said predetermined reference points are points at which leading and trailing edges of said timing pulses cross predetermined thresholds.

3. A system as recited in claim 1 wherein said controller means determines said timing error by comparing a respective current delay imposed by said delay means with the time difference between an undelayed first timing pulse and a respective undelayed second timing pulse averaged over said timing particles.

4. A system as recited in claim 1 wherein said predetermined reference points are points at which leading and trailing edges cross predetermined thresholds, said timing difference being equivalent to $((t2-t1)-(t4-t3))/2$, where t1 is the time of detection of the leading edge of the respective undelayed first detection pulse, t2 is the trailing edge of the respective undelayed first detection pulse, t3 is the leading edge of the respective undelayed second timing pulse, and t4 is the trailing edge of the respective undelayed second timing pulse.

5. A method comprising the steps of:
    illuminating a first location with radiation of a first wavelength and illuminating a second location with radiation of a second wavelength;
    flowing serially a set of timing particles past said first and second locations in that order;
    for said timing particles, generating a respective undelayed first timing pulses when said timing particles respectively reach said first location and generating respective undelayed second timing pulses when said timing particle respectively reach said second location;

using a delay device, delaying said undelayed first timing pulses to yield respective delayed first timing pulses;

determining a timing error between said delayed first timing pulses and said undelayed second timing pulses;

if said error is greater than a predetermined tolerance, adjusting said delay device to reduce said error below said tolerance;

flowing a fluorescent particle past said first and second locations in that order;

detecting fluorescence emitted by said particle so as to generate an undelayed first fluorescence pulse while said fluorescent particle is at said first location and so as to generate an undelayed second fluorescence pulse while said fluorescent particle is at said second location;

using said delay device, delaying said undelayed first fluorescence pulse; and subtracting from one of said delayed first fluorescence pulse and said undelayed second fluorescence pulse a fraction of said second pulse.

* * * * *